United States Patent
Hunter et al.

(10) Patent No.: US 7,959,292 B2
(45) Date of Patent: Jun. 14, 2011

(54) VISION SCREENER

(75) Inventors: David G. Hunter, Wayland, MA (US); Nadezhda V. Piskun, Sudbury, MA (US)

(73) Assignee: Children's Medical Center Corporation, Boston, MA (US)

( * ) Notice: Subject to any disclaimer, the term of this patent is extended or adjusted under 35 U.S.C. 154(b) by 4 days.

(21) Appl. No.: 12/294,120

(22) PCT Filed: Mar. 27, 2007

(86) PCT No.: PCT/US2007/007660
§ 371 (c)(1),
(2), (4) Date: Mar. 25, 2009

(87) PCT Pub. No.: WO2007/126873
PCT Pub. Date: Nov. 8, 2007

(65) Prior Publication Data
US 2009/0316111 A1    Dec. 24, 2009

(51) Int. Cl.
*A61B 3/00* (2006.01)
(52) U.S. Cl. ......... 351/246; 351/201; 351/202; 351/209
(58) Field of Classification Search .................. 351/201, 351/246
See application file for complete search history.

(56) References Cited

U.S. PATENT DOCUMENTS

| | | | | |
|---|---|---|---|---|
| 5,206,671 A | * | 4/1993 | Eydelman et al. | 351/203 |
| 5,812,241 A | * | 9/1998 | Doms et al. | 351/217 |
| 5,963,300 A | * | 10/1999 | Horwitz | 351/209 |
| 6,027,216 A | | 2/2000 | Guyton | |
| 6,048,064 A | * | 4/2000 | Hosoi et al. | 351/212 |
| 6,912,301 B1 | * | 6/2005 | Lin et al. | 382/128 |
| 2006/0132711 A1 | * | 6/2006 | Iwanaga | 351/208 |

OTHER PUBLICATIONS

Hunter et al. 'Pediatric Vision Screener 1: Instrument design and operation'; Journal of Biomedical Optics, 2004, vol. 9(6), p. 1363-1368.
Nassif al. 'Pediatric Vision Screener 2: pilot study in adults'; Journal of Biomedical Optics, 2004, vol. 9(6), p. 1369-1374.

* cited by examiner

*Primary Examiner* — Jessica T Stultz
(74) *Attorney, Agent, or Firm* — Altera Law Group, LLC

(57) ABSTRACT

Generally, the present invention relates to medical devices and a method of vision screening, and more particularly to a pediatric vision screening system and method thereof that identifies a risk factor for amblyopia or diagnoses amblyopia by measurement of microstrabismus. An embodiment of the invention is directed to a method of patient screening for risk factors for amblyopia which includes the steps of illuminating the eye with polarized light, scanning the polarized light about the eye, capturing the retro-reflected light emanating back from the eye, analyzing the retro-reflected light to determine ocular misalignment; and calculating a metric to determine if the patient passes or fails the screening test thereby providing an indication that the patient may have a risk of amblyopia based on either strabismus or anisometropia. The method is effective at detecting amblyopia related to focusing problems without the measuring the focus of the eye directly.

24 Claims, 3 Drawing Sheets

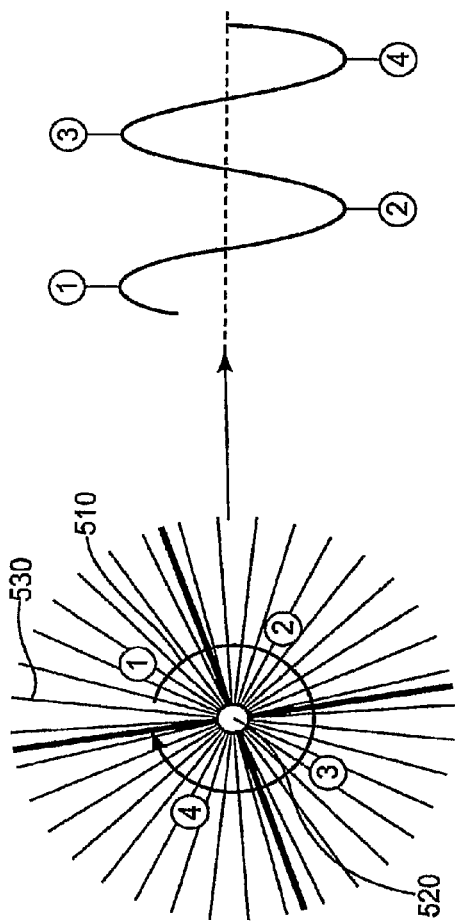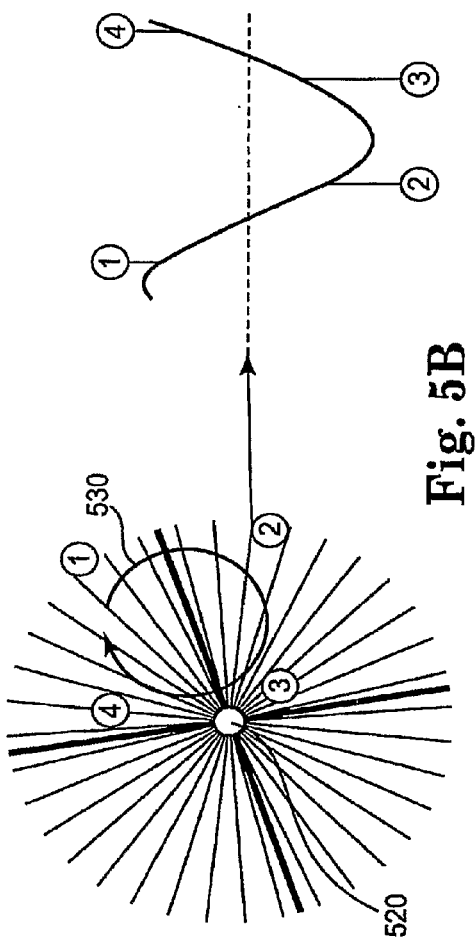

VISION SCREENER

FIELD OF THE INVENTION

The present invention is directed generally to medical devices and a method of vision screening, and more particularly to a pediatric vision screening system and method thereof that identifies a risk factor for amblyopia by measurement of microstrabismus.

BACKGROUND

Amblyopia is defined as poor vision in a structurally sound eye, and with a prevalence of 3-5%, it is the leading cause of vision loss in childhood. Amblyopia results from the inability of the brain to correctly interpret visual input due to deprivation or suppression. Anatomical risk factors for this condition include strabismus, anisometropia, cataract, certain forms of astigmatism, and hyperopia. Early detection and treatment is essential to prevent irreversible vision loss, but the risk factors can be difficult to detect. While comprehensive eye exams have been mandated in some areas, in most cases this solution is not economically feasible and tends to be instituted later than is optimal for amblyopia detection. Ideally, all children would be screened for amblyopic risk factors before age 4 or 5.

Practical vision screeners with sufficiently high testability, sensitivity, cost effectiveness, speed and specificity to reliably identify children at risk for amblyopia have been difficult to implement. Visual acuity tests have been the most widely used approach to vision screening. However, visual acuity testing may be no better than other screening tests for detecting amblyopia.

Guyton, Hunter, et. al., in U.S. Pat. No. 6,027,216 (hereby incorporated by reference) disclose a method of eye fixation monitoring using retinal reflections of polarized light to determine foveal fixation. This system was designed to detect both ocular focus and alignment. The object of the PVS is to provide a first-stage screening device that will differentiate between children in need of referral to an ophthalmologist and those not at risk, without attempting diagnosis. The output of the device is binary (either "refer" or "pass") to facilitate use by non-ophthalmologists.

SUMMARY OF THE INVENTION

Generally, the present invention relates to medical devices and a method of vision screening, and more particularly to a pediatric vision screening system and method thereof that identifies a risk factor for amblyopia by measurement of microstrabismus.

An embodiment of the invention is directed to a method of patient screening for risk factors for amblyopia which includes the steps of illuminating the eye with polarized light, scanning the polarized light about the eye, capturing the retro-reflected light emanating back from the eye, analyzing the retro-reflected light to determine ocular misalignment; and calculating a metric to determine if the patient passes or fails the screening test thereby providing an indication that the patient may have a risk of amblyopia based on either strabismus, anisometropia, or any other eye condition that might interfere with the focus or alignment of the eyes.

Another embodiment of the invention is directed to a method of patient screening for risk factors for amblyopia which includes the steps of illuminating the eye with polarized light, scanning the polarized light about the eye, capturing the retro-reflected light emanating back from the eye, analyzing the retro-reflected light to determine ocular misalignment; and calculating a metric to determine if the patient passes or fails the screening test thereby providing an indication that the patient may have a risk of amblyopia derived from anisometropia. Another embodiment is to actually diagnose the condition of amblyopia rather than simply detect the risk for amblyopia. This can be used to follow the response to treatment, or to distinguish between patients who may have risk factors but have not developed the condition vs. patients with or without measurable risk factors who have developed the condition.

Another embodiment of the invention is directed to an apparatus for screening children for risk factors for amblyopia including an optical source for illuminating the eye, a polarizer to filter the output of the optical source, a scanner configured to direct the polarized light about the human eye at an oblique angle to the eye and at an angular frequency, an optical channel to capture the retro-reflected light from the eye and route the retro-reflected light to an optical detector, a calculator to compute the binocularity score based on the captured data, and an output device to indicate pass or fail if the binocularity score exceeds, or fails to exceed, a predetermined threshold.

The above summary of the present invention is not intended to describe each illustrated embodiment or every implementation of the present invention. The figures and the detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 5A depicts an optical beam scanned in a circular pattern on the retina surface of a human eye encompassing the fovea region of the retina.

FIG. 5B depicts an optical beam scanned in a circular pattern on the retina surface of a human eye not encompassing the fovea region of the retina.

Figure 1:
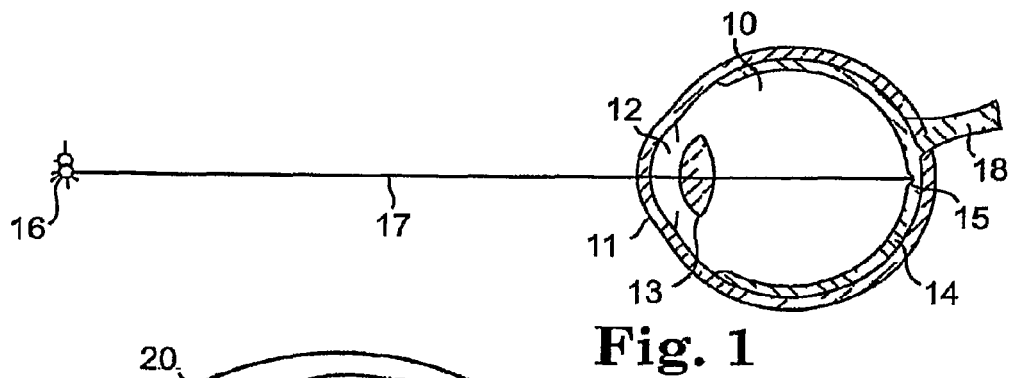
FIG. 1 is a cross sectional view of a human eye.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

In general, the present invention is directed to medical devices and more particularly to a pediatric vision screening system that identifies a risk factor for amblyopia by measurement of microstrabismus. What follows is an overview of the optical measurement technique to detect ocular misalignment (strabismus).

The human eye has birefringent properties that may alter the state of polarization of an incoming optical beam traversing and ultimately retro-reflected from the retina region of the eye. The eye serves best as a retro-reflector when the eye is focused in the same plane, and nearly boresighted to, the incoming optical beam. In this case, an image of the source of light is formed on the central region of the retina, wherein the majority of the reflection in the eye takes place. Reflected light from this image is focused by the optics of the eye, and directed back toward the light source. Under certain conditions the polarization state of the incoming optical beam may be modified by interacting with naturally occurring birefringent elements within the eye. The nerve fibers in the retina of the eye have this birefringent property and may alter the polarization state of light impinging on them as a function of their incident orientation. These nerve fibers are arrayed in a characteristic pattern in the retina, specifically radiating outward from the fovea and converging to the optic nerve head. By analyzing polarization related changes in retro-reflected light from multiple retinal areas of both eyes either sequentially or simultaneously, characteristic birefringence signatures of portions of the retina can be identified which can be used to assess the direction of fixation of the eye.

FIG. 1 is a cross sectional view of the human eye 10. Light incident upon the eye 10 enters through the transparent cornea 11, passes through the pupil 12, traverses the transparent crystalline lens 13, and proceeds toward the fundus region of the eye, which is the inside aspect of the back of the eye, and passes through the retina 14 which lines the inner surface of the back of the eye. A central depression in the retina identifies the fovea 15 which is the area of the retina having the most acute vision. In viewing an object 16, the brain uses the neck and eye muscles to aim the eye at the object. The direction of fixation is defined by the orientation of the axis of fixation 17 which connects the object 16 with the fovea 15 of the eye. When the eye is fixed on object 16, an image of the object 16 is formed on the fovea 15, and in a conjugate manner an image of the fovea 15 is projected onto the object 16. Further, retinal nerve fibers (see FIG. 2; element 20) arising from all parts of the retina 14 travel along the surface of the retina 14 and converge to form the optic nerve 18 which conveys visual information from the eye to the brain.

Figure 2:
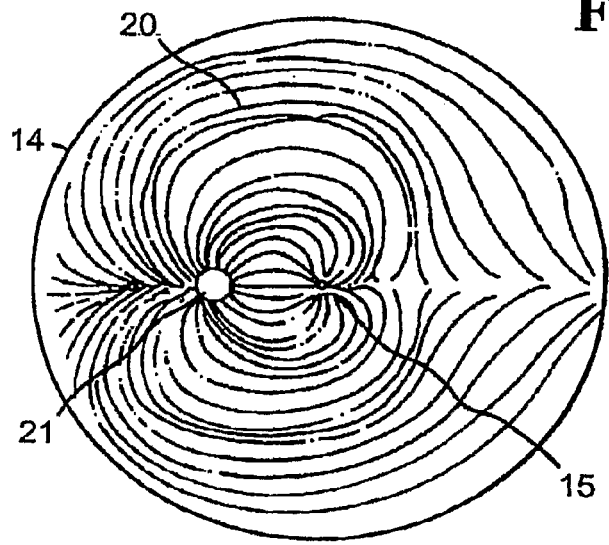
FIG. 2 is a flattened view of the posterior surface of the retina.

FIG. 2 is a flattened view of the posterior surface of the retina 14, showing the characteristic array of retinal nerve fibers 20 arising from all parts of the retina 14 and converging to the optic nerve head 21. A large fraction of the retinal nerve fibers 20 arise from the foveal area where the concentration of neural elements is greatest and vision is most acute. As the retinal nerve fibers 20 leave the foveal area, they first travel in a radial direction away from the fovea 15, then curve around as necessary to eventually reach the optic nerve head 21.

Figure 3:
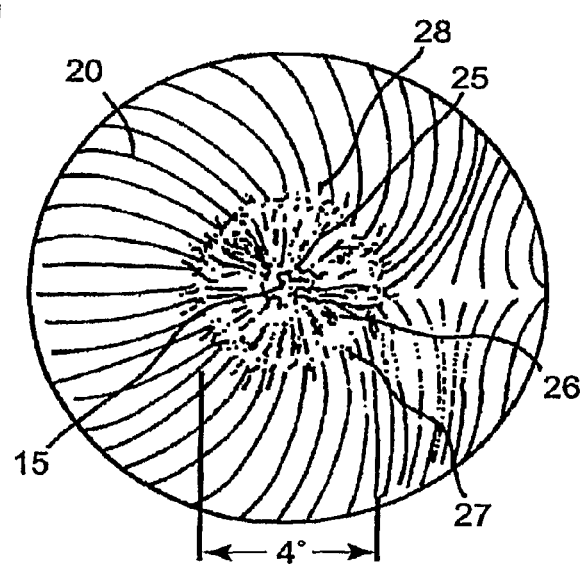
FIG. 3 is an enlarged view of the foveal area of the retina centered on the fovea.

FIG. 3 is an enlarged view of the foveal area of the retina 14, centered on the fovea 15, showing in greater detail the paths of the nerve fibers leaving the fovea 15. The cell bodies 25 of the photoreceptor elements are in the very center of the fovea 15. These cell bodies send nerve fibers called axons to communicate with a ring of ganglion cells 27 surrounding the fovea. The ganglion cells in turn give rise to long axons of their own, constituting the retinal nerve fibers 20 which travel to the optic nerve to communicate with the brain.

The short axons 26 of the photoreceptor cell bodies are called Henle fibers and emanate radially about the center of the fovea 15. This radial array of Henle fibers, ending at the ring of ganglion cells 27, has an overall diameter subtending approximately four degrees of visual angle. Besides the area surrounding the fovea, the only other location in the retina having a radial array of nerve fibers is the area around the optic nerve head. The optic nerve head 21 subtends a visual angle of about five degrees. Therefore, an area of the retina at least six or seven degrees in diameter would have to be examined in order to detect the radial pattern of nerve fibers surrounding the optic nerve head. Thus, the array of Henle fibers centered on the fovea 15, because of its relatively small angular size and its precise radial symmetry, constitutes a unique arrangement of nerve fibers within the retina and, therefore, can serve as a marker for the fovea. Therefore, identification of the location of the array of Henle fibers also identifies the location of the fovea, being centered in the array of Henle fibers.

Both the Henle fibers and the other retinal nerve fibers are birefringent, with the optical axis of the birefringence being parallel to the direction of the fiber. In general, this birefringence will change the state of polarization of polarized light that passes across the nerve fiber. Polarized light striking the retina, therefore, will be changed in its state of polarization as it passes through the layer of nerve fibers. A small fraction of the light passing through the nerve fibers is reflected by deeper layers of the fundus to pass back through the pupil of the eye. This portion of the light thus double-passes the nerve fibers, and its state of polarization is changed twice by the birefringence of the nerve fibers.

Figure 4:
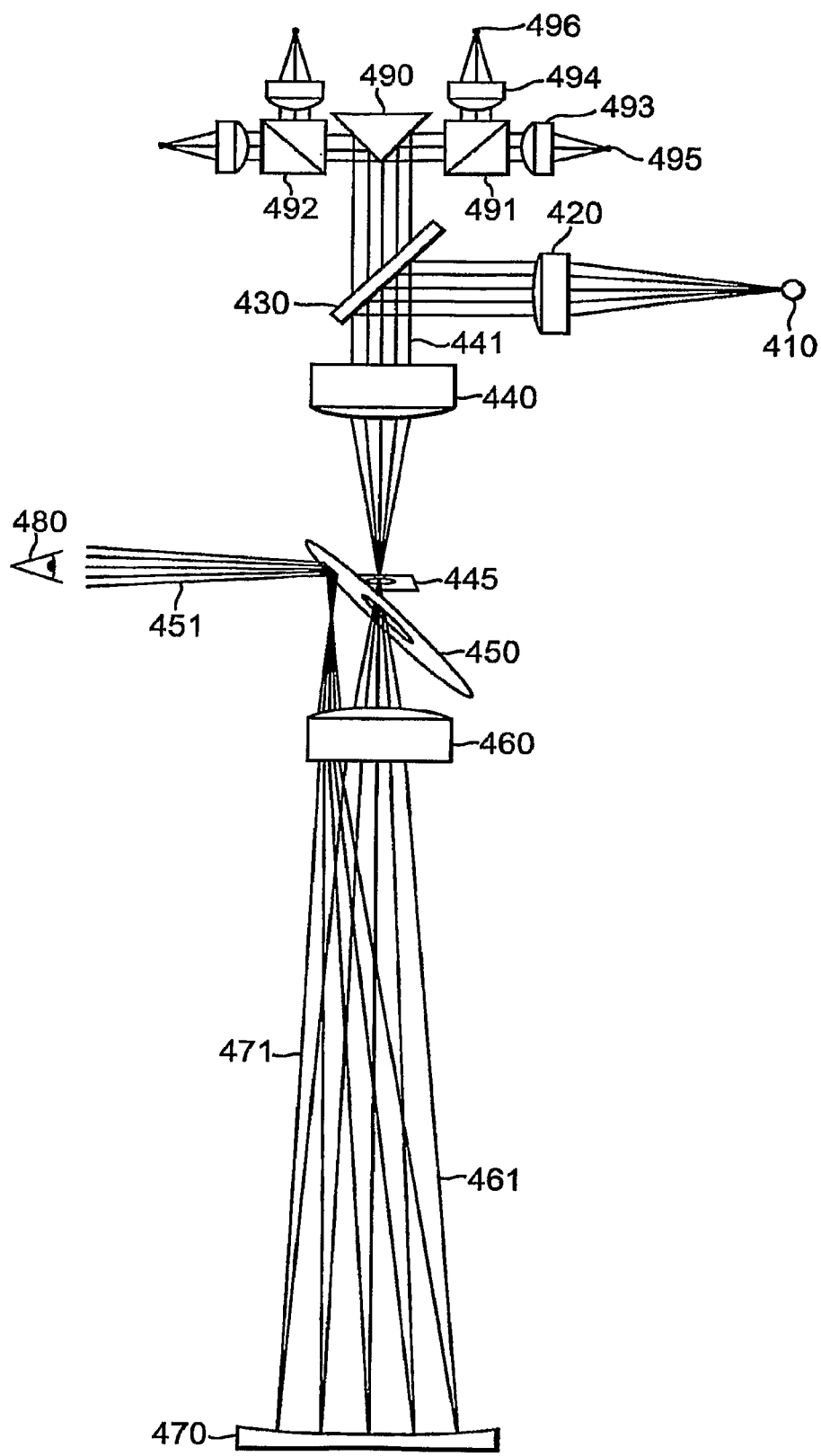
FIG. 4 is a schematic representation of one embodiment of an optical instrument which may illuminate and subsequently detect polarization related changes in optical energy retro-reflected by a human eye.

FIG. 4 is a schematic representation of one embodiment of an optical instrument 400 which may illuminate and subsequently detect polarization related changes in optical energy retro-reflected by a human eye. An optical source 410 of energy may provide a linearly polarized output which is routed to the patient's eyes by relay optics. The optical source 410 may comprise, but is not limited to, a laser, a laser diode, a light emitting diode, or a broad-band optical source such as a halogen lamp with appropriate wavelength selective filter and linear polarizer. The output of the optical source 410 may be collimated by optical lens 420 and reflected by partial beamsplitter 430. The optical beam reflected by partial beamsplitter 430 may be brought to a focus by condensing lens 440 at a location passing through aperture stop 445 and through the clear hole in mirror 450, which may be oriented at 45 degrees relative to the incoming optical beam. The optical beam diverging from mirror 450 may be collimated by lens 460 enroute to mirror 470. Mirror 470 may be tilted slightly off axis relative to incoming beam 461 such that reflected beam 471 returns to lens 460 displaced laterally a sufficient amount to be focused back onto the reflective surface of mirror 450. The reflected beam 451 from mirror 450 is thereby incident upon the patient eyes 480. The tilted mirror 470 may be rotated at angular frequency $\Omega$ (omega) about its axis of symmetry such that the incident optical beam 451 impinging upon the patient's eyes may map out a circular arc when ultimately focused on the patient's retina (see FIG. 5). The retro-reflected signal emanating from the patient's eye is reflected by mirror 445 and captured by lens 460, i.e. captured in the sense that the retro-reflected signal is focused onto mirror 470 by lens 460 in such a manner as to retrace the path of incoming optical beams 451, 471, and 461 in this order eventually passing through the central hole in mirror 450 enroute to lens 440. The reason that the retro-reflected signal retraces the illumination pathway is that the optical channel to capture the retro-reflected signal, composed primarily of mirrors 445 and 470 and lenses 460 and 440, is that the illumination and capture optics are designed to be optically conjugate. After recollimation by lens 440, a fraction of beam 441 is transmitted by partial beam splitter 430 enroute to knife edge reflecting prism 490. Knife edge reflecting prism 490 spatially separates the retro-reflected signal from the patient's left and right eyes enroute to polarizing beam splitters 491 and 492. Polarizing beam splitter 491 spatially separates the input beam from one eye (say, the right eye for example) into its' orthogonal x and y polarized components which are then focused by condensing lens 493 and 494 onto separate optical detectors 495 and 496. In one embodiment of the present invention, the electronic outputs of optical detectors 495 and 496 are subtracted from one another to produce a differential polarization (X–Y) output insensitive to common mode specular reflections and non-polarized light. The optical beam incident upon polarizing beam splitter 492, for the left eye, is processed similar to that of beamsplitter 491 outlined above. The output of optical detector 495 (and 496) may be analyzed in the frequency domain as outlined below to determine if the patient is fixated within an acceptable offset angle relative to the incident optical beam 451.

With reference to FIGS. 5A and 5B, when the patient's eye is fixating directly at the incoming optical beam (FIG. 4, element 451), the circular arc mapped out by way of rotating mirror 470, forms a circular arc 510 centered about the fovea region 520 and subtending approximately 3° of the patient's angular field of view. FIG. 5A depicts a view of the Henle fibers 530 radially expanding from the fovea region 520. The Henle fibers 530 exhibit form birefringence wherein a principal axis of each fiber lines along the direction of its' radial path. When interacting with polarized light, each individual Henle fiber may alter the state of polarization of an incident linearly polarized beam by an amount depending upon the vector angle between the incident beam's polarization vector relative to the fiber's principal axis. Locations 1 through 4 in FIG. 5A represent one representative clockwise circular arc generated by rotating mirror 470, wherein the arc encompasses the fovea region 520. Similarly, FIG. 5A-1 maps in the time domain a one-to-one relationship of locations 1 through 4 in the circular arc to the electronic signal generated by the differential polarization output (X–Y) described earlier. As can be seen, in one revolution of the arc 510 about the fovea at angular frequency $\Omega$, the time domain differential polarization signal (X–Y) generates a $2\Omega$ (frequency doubled) component. In contrast, FIG. 5B depicts one representative clockwise circular arc generated by rotating mirror 470, wherein the patient's eye is skewed off axis relative to the incoming optical beam 451 by a sufficient amount that the circular arc lies outside and does not encompass the fovea region 520. In this case the one-to-one mapping in the time domain generates a time domain differential polarization signal (X–Y) at the same angular frequency $\Omega$ as the rotating mirror 470. Given this, the differential polarization signal can be analyzed by frequency spectrum analysis to detect the presence, or absence; of the $2\Omega$ frequency doubled signal which can be used to determine if the patient's eye is within a particular angular offset relative to the incoming optical beam 451. For example, fast fourier transform techniques can be used to analyze the ratio of the $1\Omega$ to $2\Omega$ signal strength and a predetermined threshold for this ratio may be established in clinical trials to establish a pass/fail ("refer") criterion for the test.

Instrumentation similar to that as described in FIG. 4 was used to evaluate the clinical performance of screening children for strabismus in a pediatric ophthalmology office setting. In one study 77 subjects between 2 and 18 years of age received "gold standard" orthoptic examinations, and were classified as "at risk" for amblyopia if strabismus or anisometropia (greater than 1.50 diopters difference) was present. Strabismus was sub-classified as variable or constant. The subjects were then tested with the instrumentation, a metric termed the binocularity score was calculated from the collected data (see equation below) and a pass or fail recommendation based upon the binocularity score was assessed. If the calculated binocularity score met or exceeded a predetermined threshold the subject was considered to have passed the screening test, otherwise the subject was considered to have failed the test and may be referred for follow-on testing (the failed subject being coined a "refer"). During central fixation, the incoming light beam to the eye (see FIG. 4; element 451) is focused by the eye and surrounds the fovea, as illustrated by the circle centered on the fovea shown in FIG. 5A. The device measures the number of times in a series of five measurements that the subject is able to binocularly fixate and produces a binocularity score as a percentage, wherein binocularity was calculated as:

$$\text{Binocularity} = \frac{\text{Number of bilateral readings}}{\text{Number of unilateral readings} + \text{Number of bilateral readings}} \times 100\%$$

Thus binocularity included only those readings in which at least one eye was fixating on the target. A subject who was relatively inattentive to the target did therefore not influence this parameter. If neither eye was centrally fixating, the reading was not included in the binocularity calculation. That is, a subject with 100 percent binocularity had bilateral alignment for every usable reading. Based on the results of a pilot study in adults, a binocularity score of greater than 60% was defined as "passing."

In the first study, measurements were obtained from 77 children, 40 of whom had risk factors for amblyopia. Given the above criterion of a binocularity score greater than 60% as passing, all control subjects (n=37) received a passing score. Subjects were considered "control" if there they had no history of major ocular problems, and if both eyes met all of the following criteria: less than 3.25 diopters of myopia, less than 3.25 diopters of hyperopia, less than or equal to 1.50 diopters of anisometropia, and no strabismus. No separate criterion was set for astigmatism. Also, the results of this study yielded a binocularity score of less than 20% (a "refer") for all subjects with constant strabismus and subjects with variable strabismus had binocularity scores ranging from 0% to 52% (also a "refer"). In addition, the 3 subjects pre-screened with anisometropia, and no strabismus, were all tested to have a binocularity score less than 10%. Follow-on testing with an additional 8 subjects pre-screened with anisometropia (7 of which with greater than 1.5 diopters difference), and no strabismus, yielded similar results with all subjects with anisometropia greater than 1.5 diopters having a binocularity score less than 60%. Given these results, the binocular retinal birefringence scanning technique may be directly sensitive to anisometropia, a risk factor for amblyopia. One possible explanation for these results may be that a sufficient focus in both eyes is a prerequisite for accurate fixation. To achieve a passing binocularity score, a subject must be able to focus and fixate on the target simultaneously with both eyes. However, a subject with anisometropia has one eye severely out of focus, which may impair the accuracy of fixation in that eye, leading to low binocularity Score. For example, the lack of fixation (meandering) may mimic the effect of lack of binocular alignment, but the scores on successive scans may be substantially different from each other. This may give clues that the risk factor is not binocular alignment but anisometropic induced meandering. For the screener, it does not matter. The goal is to rapidly identify subjects at risk for further evaluation. An acuity test given to a small group of selected subjects, who are suspected of being at risk for amblyopia is far simpler and more cost effective than testing every subject for acuity. This effect may be understood by examining the binocularity score equation shown below $$\text{Binocularity} = \frac{\text{Number of bilateral readings}}{\text{Number of unilateral readings} + \text{Number of bilateral readings}} \times 100\%$$

One possible explanation is that the defocused spot on the retina in the anisometropic eye is sufficiently large so as to generate a significant amount of 1Ω signal at the mirror scanning frequency (see FIG. 5B) during the cyclical scans so as to be designated as a unilateral reading (i.e., one good reading via the 2Ω signal from the in-focus eye). The large 1Ω (unilateral) term may directly drive down the binocularity score leading to the patient being "referred" to follow-on treatment. Alternatively, the anisometropic eye, unable to effectively focus, may wander throughout the procedure, generating a mixture of 2Ω signal while on or near axis, but generating a sufficient amount of 1Ω signal while wandering off axis to bias the result to a unilateral score, again driving down the binocularity score leading to the patient being "referred". The present invention also contemplated the use of statistical analysis techniques applied to multiple determinations of the binocularity score as described above. Here, the protocol established above may be repeated multiple times and a mean and standard deviation may be calculated from the data set of individual binocularity scores. This test protocol may be useful in determining if eye wandering, whether random or induced by lack of fixation via an anisometropic eye, may influence the repeatability of the binocularity score. Furthermore, statistical non repeatability may itself set a threshold for identifying the patient as having a risk factor for amblyopia. For example, if the deviations in the binocularity scores vary by more than 2 standard deviations from the mean binocularity score, the patient may be indicating a probability of a risk factor for amblyopia. An alternative criterion may be, if the standard deviation of repetitive binocularity scores exceeds a predetermined clinically established threshold, the patient may be indicating a probability of a risk factor for amblyopia.

The instrumentation as described in FIG. 4 may also be designed with additional optical components that can assess the patient's ability to fixate and focus on a target. The focus detection characteristics of the instrumentation have been published elsewhere (see Hunter et. al., "Automated detection of ocular focus", Journal of Biomedical Optics, 2004, 9:1103-1109) which is incorporated in its entirety herein by reference. However, given the above results, it may be possible to screen children for risk factors for amblyopia by measurement of microstrabismus alone, without the need for simultaneous or follow-on visual acuity/focusing data. As a result, it is possible to determine subjects at risk of amblyopia by testing for binocular misalignment (strabismus) as set forth above, but without the need to explicitly test for anisometropia (focal differential between eyes). This permits the development of a faster and cheaper screening device than was heretofore possible. Given this, a single test (binocular retinal birefringence scanning) may directly identify one risk factor for amblyopia and indirectly identify another (anisometropia); the device required may thus be simpler than first imagined. Furthermore, because mass screening must be done quickly, by using one test, the time required to achieve results may be reduced. In future embodiments of screening devices, optimization of this single test will undoubtedly result in even faster screening with higher patient throughput.

In some cases, the binocularity score returned to normal after treatment of amblyopia improved visual acuity to within the normal range. In other cases, patients with potential risk for amblyopia (but no amblyopia) had normal binocularity scores. This suggests that the detection of microstrabismus in association with amblyopia may diagnose the condition of amblyopia rather than simply detecting conditions that place the patient at risk for amblyopia.

As noted above, the present invention is applicable to medical devices and is believed to be particularly useful for screening children (pediatric) for risk factors for amblyopia because this screening technique requires very little co-operation of the patient and no patient response or interaction is required. This is particularly advantageous in pediatric screening of very young children. The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the present specification. The claims are intended to cover such modifications and devices.

We claim:

1. A method of detection of microstrabismus in order to diagnose amblyopia, comprising the steps of:
    a) illuminating the eye with polarized light;
    b) scanning the polarized light about the eye;
    c) capturing the retro-reflected light emanating back from the eye;
    d) analyzing the retro-reflected light to determine ocular misalignment without measuring for focus; and
    e) calculating a metric to determine if the patient has evidence of microstrabismus which thereby diagnoses amblyopia.

2. The method of claim 1 wherein the polarized light is linearly polarized.

3. The method of claim 1 wherein the polarized light is circularly polarized.

4. The method of claim 1 wherein scanning the polarized light includes periodic rotation of light at a predetermined oblique angle to the eye and at a predetermined angular frequency.

5. The method of claim 4 wherein scanning the polarized light includes periodic rotation of light at a predetermined oblique angle to the eye and at a predetermined angular frequency delivered to both eyes simultaneously.

6. The method of claim 4 wherein scanning the polarized light includes periodic rotation of light at a predetermined oblique angle and a predetermined angular frequency delivered to both eyes sequentially.

7. The method of claim 1 wherein capturing the retro-reflected light includes an optical detector disposed optically conjugate to the light source and the eye.

8. The method of claim 1 wherein analyzing includes polarization filtering of the retro-reflected light into orthogonal components.

9. The method of claim 8 wherein analyzing includes subtracting the filtered orthogonal polarization components.

10. The method of claim 1 wherein analyzing includes comparing the frequency spectrum of the retro-reflected light to the angular frequency of light incident upon eye.

11. The method of claim 1 wherein calculating the ocular misalignment of the eye includes determining whether the angular offset exceeds a predetermined threshold value.

12. The method of claim 1 wherein the metric is a binocularity score given by $$\text{Binocularity} = \frac{\text{Number of bilateral readings}}{\text{Number of unilateral readings} + \text{Number of bilateral readings}} \times 100\%.$$

13. The method of claim 12 wherein a predetermined minimum threshold above which is needed to classify the patient as "passed", otherwise "refer".

14. The method of claim 1 wherein the step of calculating the metric is conducted multiple times and further includes the step of detecting a lack of eye fixation, indicating the possibility of anisometropia.

15. The method of claim 14 wherein calculating non repeating binocularity scores indicates a risk factor for anisometropia.

16. The method of claim 15 wherein if said non repeating binocularity scores exceed a predetermined clinically established threshold, the patient is indicating a risk factor for amblyopia.

17. The method of claim 15 wherein a mean value and standard deviation is calculated from multiple binocularity scores.

18. The method of claim 15 wherein if the deviations in the binocularity scores vary by more than 2 standard deviations from the mean binocularity score, the patient is indicating a probability of a risk factor for amblyopia.

19. The method of claim 15 including the step of calculating the variability in repetitive binocular score determinations and if the standard deviation of repetitive scores exceeds a predetermined clinically established threshold, the patient is indicating a probability of a risk factor for amblyopia.

20. A method of detection of microstrabismus in order to diagnose amblyopia, comprising the steps of:
   a) illuminating the eye with polarized light;
   b) scanning the polarized light about the eye;
   c) capturing the retro-reflected light emanating back from the eye;
   d) analyzing the retro-reflected light to detect eye wandering without measuring focal differential between eyes; and
   e) calculating a metric to determine if the patient has evidence of microstrabismus which thereby diagnoses amblyopia.

21. The method of claim 20 wherein the step of calculating includes performing scan to scan frequency spectrum analysis.

22. The method of claim 21 wherein frequency spectrum analysis includes fast Fourier transform techniques.

23. The method of claim 20 wherein the step of calculating includes repetitive binocular score determinations.

24. The method of claim 21 including the step of calculating the ratio of the captured signal at the scanning frequency to the captured energy at the frequency doubled scanning frequency, and if the ratio does not exceed a predetermined clinically established threshold, the patient is indicating a probability of a risk factor for amblyopia.

* * * * *